United States Patent [19]

McConnell

[11] Patent Number: 4,730,609

[45] Date of Patent: Mar. 15, 1988

[54] SURGICAL DRAPE WITH LIMB SECURING STRUCTURE AND METHOD FOR SECURING A SURGICAL SITE

[76] Inventor: Bernard E. McConnell, Rte. 2, Box 87, Greenville, Tex. 75401

[21] Appl. No.: 706,346

[22] Filed: Feb. 27, 1985

[51] Int. Cl.⁴ .................... A61B 17/56; A61B 19/08
[52] U.S. Cl. ............................................. 128/132 D
[58] Field of Search ................. 128/132 D; 206/440

[56] References Cited

U.S. PATENT DOCUMENTS

| | | | |
|---|---|---|---|
| 1,554,692 | 9/1925 | Shane | 128/132 D |
| 3,060,932 | 10/1962 | Pereny et al. | 128/132 D |
| 3,423,277 | 1/1969 | Dipner | 128/132 D |
| 3,889,667 | 6/1975 | Collins | 128/132 D |
| 3,930,497 | 1/1976 | Krebs et al. | 128/132 D |
| 4,119,093 | 10/1978 | Goodman | 128/132 D |
| 4,524,767 | 6/1985 | Glassman | 128/132 D |

FOREIGN PATENT DOCUMENTS 51935  5/1982  European Pat. Off. ........ 128/132 D

Primary Examiner—Richard T. Stouffer
Attorney, Agent, or Firm—Dennis T. Griggs

[57] ABSTRACT

An improved surgical drape form maintaining a sterile condition about a selected surgical site on a body portion of a patient during a surgical procedure such as hip surgery and the like. The surgical drape comprises generally a sheet of conformable, impervious material having an opening for receiving the patient's limb and having side portions adjoining the opening for shielding the patient with respect to direct contact and ambient air flow. A boot of conformable impervious material is attached to the sheet for receiving the patient's limb. The boot has a tubular sidewall defining a pocket which is joined in registration with the sheet opening. The tubular sidewall is sealed against the sheet portions forming the border of the opening, thereby providing a continuous, sterile barrier.

8 Claims, 3 Drawing Figures

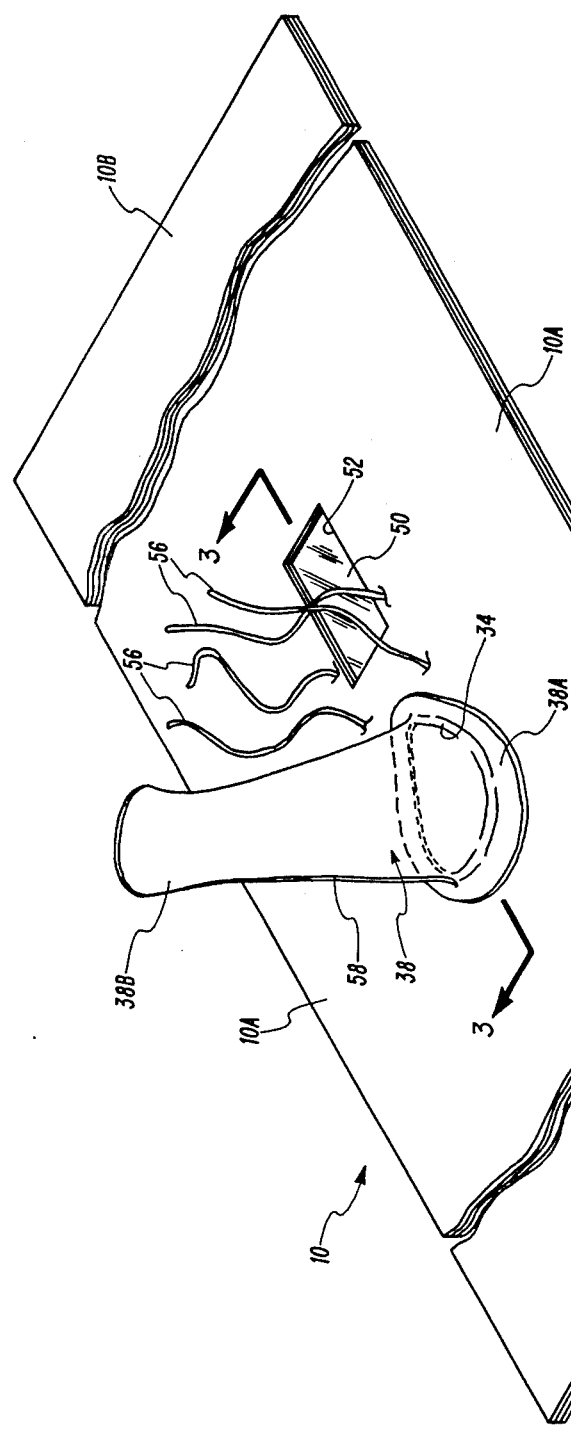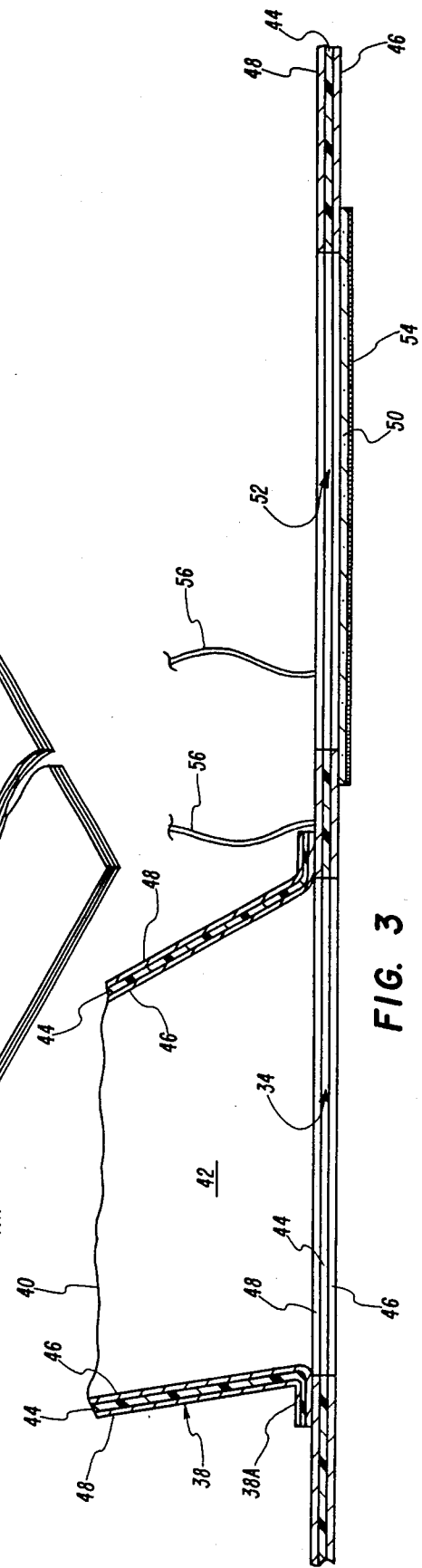

SURGICAL DRAPE WITH LIMB SECURING STRUCTURE AND METHOD FOR SECURING A SURGICAL SITE

FIELD OF THE INVENTION

The present invention relates generally to surgical drapes, and in particular to a disposable, sterile drape for covering a patient's extremity during a surgical procedure such as hip surgery and the like.

BACKGROUND OF THE INVENTION

In the performance of orthopedic surgery and related procedures, sterile operating conditions are maintained by a surgical drape which covers the patient and the operating table. The surgical procedure is performed through a slit or preformed fenestration which is aligned with the desired surgical site. It is sometimes necessary to support a portion of the patient's body including one or more limbs in an elevated position during the procedure, and also to vary the position of the limb or body portion from time to time. During hip surgery, for example total hip replacement, sub-capital fractures of the hip in which a prosthesis is implanted, and arthrotomy of the hip, it is necessary to manipulate the leg, including movements involving abduction-adduction, flexion-extension, internal and external rotation of the limb.

It will be appreciated that such movements may disturb the established position of the drape, and as a result, may interfere with the surgical procedure. Because of its proximity to the selected surgical site on the hip, the patient's leg must remain covered by the drape or other such sterile barrier to maintain the sterile condition of the selected surgical site.

DESCRIPTION OF THE PRIOR ART

According to prior practice, the patient assumes a lateral or anterior reclining position upon an operating table and is completely covered by a large, sterile drape. The surgical procedure is performed through an opening, or fenestration, formed in the drape itself. The limb is manipulated while covered by the surgical drape. In some cases, operating room personnel manually support the extremity and manipulate it as required. Because the limb is handled while it is covered by the surgical drape, the position of the drape is disturbed and movement of the drape may produce a pumping effect which draws ambient air toward the selected surgical site. Although the air circulated through the operating room is filtered and purified, and care is taken to induce a laminar air-flow across the operating table, there is an ever-present risk of exposure of the selected surgical site to airborn pathogenic organisms.

Additionally, the fenestration through which the surgical procedure is performed is desirably kept as small as possible, and any movement of the drape will disturb the alignment of the fenestration with the selected surgical site. Contact with the limb during manipulation is indirect with the limb being continuously covered by the surgical drape. It will be appreciated that such manipulation is awkward when the limb is covered by the large, sterile drape and that considerable care must be exercised to prevent movement of the fenestration with respect to the sterile surgical site.

Adhesive strips are sometimes employed to bond the drape to the desired surgical site. Such adhesive strips are subject to being pulled away as a result of movements of the limb of the kind described above.

SUMMARY OF THE INVENTION

The present invention provides an improved surgical drape for maintaining a sterile condition about a selected surgical site on a body portion of a patient during a surgical procedure such as hip surgery and the like. The surgical drape comprises generally a sheet of conformable, impervious material having an opening for receiving the patient's limb and having side portions adjoining the opening for shielding the patient with respect to direct contact and ambient air flow. A boot of conformable impervious material is attached to the sheet for receiving the patient's limb. The boot has a tubular sidewall defining a pocket which is joined in registration with the sheet opening. The tubular sidewall is sealed against the sheet portions forming the border of the opening, thereby providing a continuous, sterile barrier.

In the preferred embodiment, the surgical drape includes a conformable panel portion having an adhesive deposit for bonding the panel portion directly onto the selected body portion at the desired surgical site. The conformable panel portion is preferably a sheet of transparent polymer material and the incision is made directly through the transparent panel which defines a sterile operating window. The position of the drape relative to the conformable, transparent panel is stabilized by one or more tie straps which secure the drape about the patient's limb at a location intermediate the boot and the sterile surgical site.

According to the preferred method, the patient assumes a lateral reclining position upon the operating table, and the desired surgical site (for example, the hip) is rendered sterile. A sterile boundary is formed around the sterilized surgical site by sterile towels. The improved surgical drape of the invention is then unfolded along the sterile zone of the operating table, with the conformable transparent panel being aligned generally with the sterile surgical site. The conformable operating panel is then adhesively bonded directly onto the sterilized skin surface at the surgical site. Next, the leg is retracted by a bending movement at the knee, and the thigh is rotated toward the chest, thereby aligning the patient's foot with the opening of the boot. The foot and leg are than inserted into the sterile boot.

The tubular sidewall material of the boot is gathered about the union of the boot and drape. Thereafter, the sheet material of the surgical drape together with material gathered from the sterile boot is securely fastened by tie straps about the thigh at a point just above the patient's knee. The tie straps effectively anchor the surgical drape to the patient's thigh at a point intermediate the boot and the selected surgical site, thereby effectively decoupling the operating window panel with respect to movements of the patient's leg.

The superior features and advantages of the present invention will be further appreciated by those skilled in the art upon reading the detailed description which follows in conjunction with the attached drawings.

BRIEF DESCRIPTION OF THE DRAWINGS

FIG. 2 is a perspective view of the improved surgical drape illustrated in FIG. 1, and;

FIG. 3 is a sectional view of the improved surgical drape taken along the lines 3—3 of FIG. 2.

DETAILED DESCRIPTION OF THE PREFERRED EMBODIMENT

Figure 1:
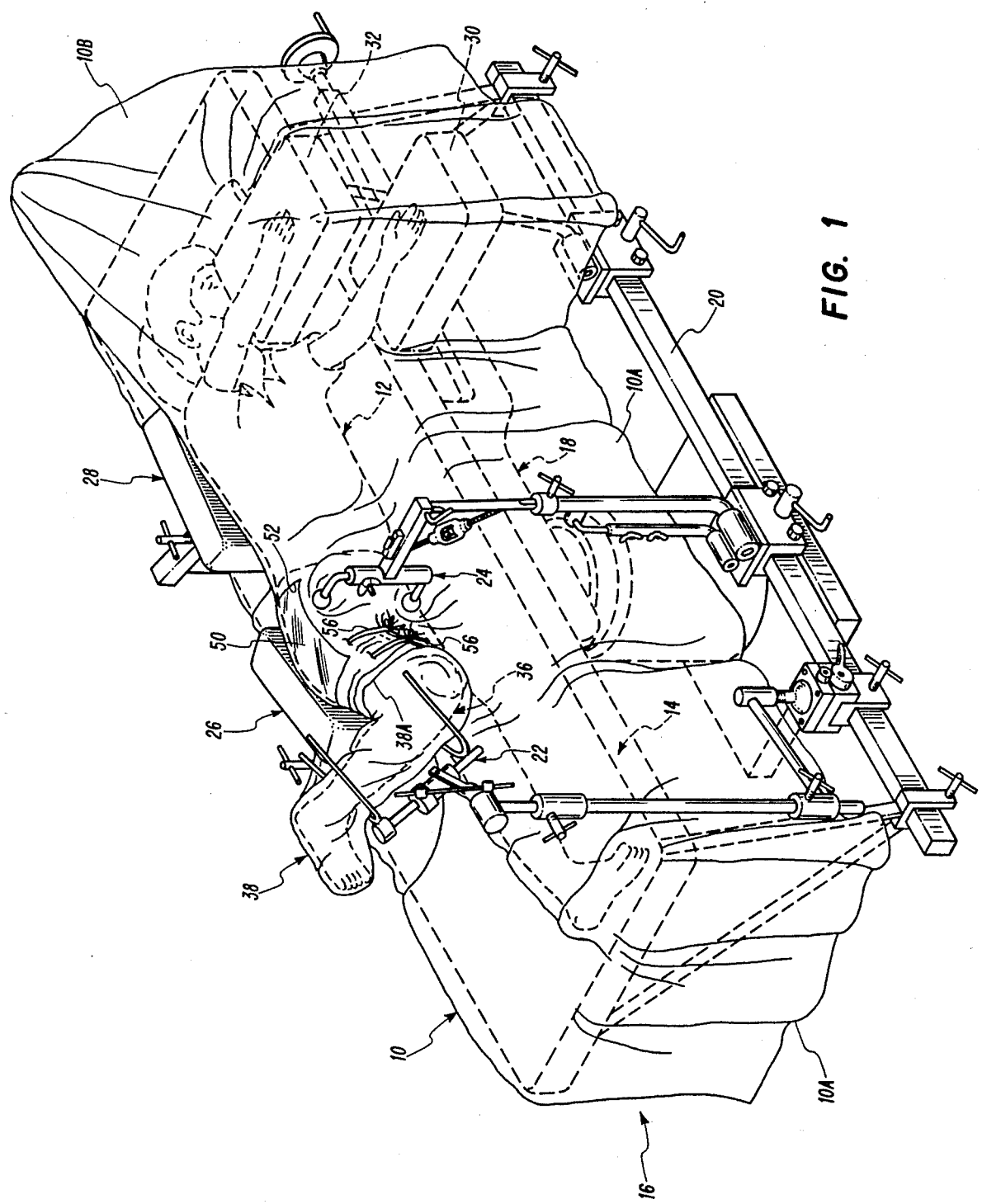
FIG. 1 is a perspective view of the improved surgical drape of the present invention as used in combination with an operating table, showing a patient in the lateral position as prepared for hip surgery.

In the description which follows like parts are indicated throughout the specification and drawings with the same reference numerals, respectively. The drawings are not necessarily to scale and certain parts have been exaggerated to better illustrate details of the present invention.

The surgical drape of the present invention is particularly well suited for use in combination with a conventional surgical operating table during performance of surgery on a selected body portion, for example, hip surgery, in which it is necessary to rotate, flex, pull or otherwise manipulate a limb such as the patient's leg.

Referring now to FIG. 1, an improved surgical drape 10 constructed according to the teachings of the present invention is disposed in an overlying arrangement with respect to a patient 12 shown reclining in a lateral position upon a sterile pad 14 which is supported by an operating table 16. The operating table 16 includes a base structure 18 which is capable of altering the orientation of the patient to accommodate various surgical procedures.

A support rail 20 is suspended from the underside of the operating table 16 near floor level to allow conventional draping techniques without penetration of the drapes. Additionally, various patient support devices are mounted onto the support rail 20 for maintaining the lateral position of the patient 12 during the operating procedure. For example, a leg positioner assembly 22 controls the rotation and position of the femur during the hip surgery procedure. An adjustable anterior pelvic caliper 24 provides bony contact just below anterior-superior iliac spines. Rigid, three-point support of the bony pelvis is completed by a posterior sacral pad 26. The upper torso of the patient 12 is supported in the lateral position by a posterior pad 28. Torsion of the upper torso is prevented by the posterior torso pad 28 and by an anterior torso support which is combined with arm boards 30, 32. The foregoing positioning devices operate external to the surgical drape 10 to maintain true lateral orientation of the patient without compromising the sterile barrier produced by the surgical drape 10.

The improved surgical drape 10 is appropriately sized to completely cover the patient 12 and the operating table 16. Skirt portions 10A of the surgical drape hang downwardly over the sides of the operating table, thereby completely shielding the sterile portions of the operating table with respect to direct contact by operating room personnel and ambient air flow. An upper end portion 10B of the surgical drape is elevated for observation of the patient and administration of anesthetic agents and the like.

Referring now to FIGS. 2 and 3, the surgical drape 10 is formed in a laminated sheet of conformable, impervious material having an opening 34 through which the patient's leg 36 may be extended. The side portions 10A, 10B which surround the opening 34 shield the patient with respect to direct contact and ambient air flow. A boot 38 projects outwardly from the sheet portion of the drape, and has a tubular sidewall 40 which encloses a pocket 42. The pocket 42 and the surrounding sidewall 38 are joined in registration with the sheet opening 34 as can best be seen in FIG. 3. The tubular boot 38 includes a collar 38A which is adhesively bonded and sealed against the sheet portions forming the border of the opening 40, thereby providing a continuous, sterile barrier.

The drape 10 along with the boot 38 preferably comprises multiple laminations of fluid impervious and absorbent materials. In the embodiment illustrated in FIG. 3, a fluid impervious layer or lamination 44 is disposed intermediate first and second absorbent laminations 46, 48. The absorbant laminations preferably comprise a non-woven fabric material, for example "Hyloft", a trademark of Scott Paper Company. The fluid impervious layer is preferably a sheet of antistatic polyethylene material. Other materials, for example vinyl or rubber, may be used to good advantage.

According to one aspect of the invention, the surgical drape 10 includes a conformable panel portion 50 aligned with and located adjacent to the boot 38 for surface engagement directly onto the selected body portion at the desired surgical site. The conformable panel portion 50 is preferably a sheet of transparent, polymer material which is adhesively bonded to the underside of the drape 10. A rectangular window 52 is formed in the drape 10 and is substantially co-extensive with the desired surgical site. The underside of the conformable panel 50 is covered by a sterile deposit of adhesive for bonding the conformable panel directly to the surface of the skin and the desired surgical site. The surgical incision is performed directly through the conformable panel 50 with the panel being adhesively bonded directly onto the selected body portion of the patient 12.

The position of the drape and to the conformable, transparent panel 50 is stabilized by tie straps 56 which secure the drape about the patient's limb at a location intermediate the boot 38 and the sterile operating window 52.

The boot 38 is tapered from the opening 34 to a slightly flaired end portion 38B. The tubular sidewall 40 of the boot 38 is sealed along a seam 58 by an adhesive heat sealing technique.

Referring again to FIG. 1, the patient 12 assumes a lateral reclining position upon the operating table 16 and the desired surgical site on the selected body portion (for example the hip) is rendered sterile by conventional procedures. A sterile boundary is formed around the sterilized site by sterile towels. The drape 10 is then unfolded along the sterile zone of the operating table, with the conformable transparent panel 50 being aligned generally with the prepared surgical site. The conformable operating panel 50 is then adhesively bonded directly onto the sterilized skin surface at the surgical site.

While the conformable operating panel 50 is held securely in place by the adhesive deposit, the patient's leg 36 is retracted by a bending movement at the knee at the same time that the thigh is rotated toward the chest, thereby aligning the patient's foot with the opening in the boot 38. The patient's foot and leg are then inserted into the sterile boot 38. The patient's leg is then elevated and placed into the leg positioner assembly 22.

The loose tubular sidewall material of the boot is gathered and pushed toward the boot collar 38A. Thereafter, the sheet material of the surgical drape 10 together with the material gathered from the sterile boot is securely fastened by the tie straps 56 about the patient's thigh at a point just above the patient's knee. The tie straps 56 effectively anchor the surgical drape to the patient's thigh at a point intermediate the boot 38 and the selected surgical site, thereby effectively decoupling the operating window panel 50 with respect to the movements of the patient's leg. That is, the patient's leg can be moved and manipulated as required during the surgical procedure without risk of disturbing the sterile adhesive bond between the conformable panel 50 and the underlying sterile body portion. Additionally, such leg movements can be performed without creating a pumping effect which might draw contaminated ambient air toward the sterilized surgical site.

It will be apparent that the improved surgical drape 10 completely covers the patient and the sterile operating zone with a fluid-impervious sterile barrier. Additionally, the patient's extremities, including the patient's leg which adjoins the selected surgical site, is covered by the sterile barrier provided by the boot 38. The fluid impervious middle lamination of the boot and drape will prevent strike through, that is, the wetting of the drape from the inner to the outer surfaces. Moreover, the closely conforming boot allows the patient's limb to be manipulated as required without disturbing the drape portions overlying the table, and without disturbing the conformable panel which shields the selected surgical site.

Although the invention has been described with reference to a specific embodiment, and with reference to a specific hip surgery procedure, the foregoing description and application have disclosed for purposes of illustration, and are not intended to construed in a limiting sense. Various modifications of the disclosed embodiments as well as alternative applications of the invention will be suggested to persons skilled in the art by the foregoing specification and illustrations. For example various surgical procedures may be performed through an opening or fenestration without the benefit of a transparent conformable panel of the type described. Additionally, the size of the boot and the location of a fenestration or conformable panel may be modified to accommodate shoulder arthroscopy, arthroplasties, osteotomies, ligament surgery and open reduction-internal fixations of fractures about the knee. It is therefore comtemplated that the apended claims will comprehend any such modifications or embodiments that fall within the true scope of the invention.

What is claimed is:

1. An improved drape for covering a patient during a surgical procedure comprising, in combination:
    a covering sheet of conformable material having a first opening for receiving a patient's limb or other body extremity and having portions adjoining said first opening for shielding the patient with respect to direct contact and ambient air flow, and said sheet of conformable material having a second opening defining a window for framing a surgical site on a selected body portion of said patient;
    a boot of conformable material attached to said covering sheet about the periphery of said first opening, said boot having a tubular sidewall defining a pocket for receiving a patient's limb adjoining the selected surgical site, said boot pocket being disposed in registration with said first sheet opening and said tubular sidewall being sealed to the covering sheet portions forming the peripheral border of said first opening;
    a panel of transparent, flexible material attached to said covering sheet and disposed coextensive with said window defined by said second sheet opening; and,
    a tie strap attached to said covering sheet at a location intermediate said boot and said window panel for securing said covering sheet about the patient's limb.

2. An improved surgical drape as defined in claim 1, said transparent panel having an adhesive deposit for bonding said panel directly onto the skin surface of the patient's body portion at the selected surgical site.

3. An improved surgical drape as defined in claim 1, said transparent panel comprising a liquid impervious polymer sheet which is adhesively bonded to said covering sheet.

4. An improved surgical drape as defined in claim 1, said covering sheet and said boot comprising a first lamination of absorbent material, a second lamination of absorbent material and a third lamination of impervious material disposed intermediate said first and second laminations.

5. A method for maintaining a surgical site on a selected body portion of a patient in sterile condition during a surgical procedure in which a limb of the patient adjoining the selected body portion is manipulated, comprising the steps:
    sterilizing the desired surgical site on the selected body portion;
    forming a sterile boundary about the sterilized surgical site;
    covering the sterilized surgical site with a conformable, transparent panel;
    covering the patient's skin surface surrounding the transparent panel with a sterile drape;
    aligning the patient's limb with the opening of a sterile boot;
    inserting the patient's limb into the sterile boot; and,
    securing the surgical drape by tie straps about the patient's limb at a location intermediate the boot and conformable transparent panel.

6. A method for maintaining a surgical site on a selected body portion of a patient in sterile condition during a surgical procedure as set forth in claim 5, wherein the patient's limb adjoining the selected body portion is one of the patient's legs, said method including the steps of rotating the patient's leg by a bending movement at the knee, rotating the patient's thigh toward the patient's chest, aligning the patient's foot with the opening of the sterile boot, and thereafter inserting the patient's foot and leg into the sterile boot.

7. A method for maintaining a surgical site on a selected body portion of a patient in sterile condition during a surgical procedure as set forth in claim 5, including the step of adhesively bonding said conformable, transparent panel directly onto the patient's skin surface at the selected surgical site within the sterile boundary.

8. A method for maintaining a surgical site on a selected body portion of a patient in sterile condition during a surgical procedure as set forth in claim 5, including the steps of gathering the boot about the union of the boot and drape, and thereafter carrying out the securing of the surgical drape by tying the gathered material with the tie straps such tying being performed about the patient's limb at a location intermediate a joint of the patient's limb and the surgical site.

* * * * *

UNITED STATES PATENT AND TRADEMARK OFFICE
CERTIFICATE OF CORRECTION

PATENT NO. : 4,730,609

DATED : 3/15/88

INVENTOR(S) : Bernard E. McConnell

It is certified that error appears in the above-identified patent and that said Letters Patent is hereby corrected as shown below:

In the Abstract - Line 1, "form" should be -- for --.

Signed and Sealed this

Sixteenth Day of August, 1988

Attest:

DONALD J. QUIGG

*Attesting Officer*    *Commissioner of Patents and Trademarks*